United States Patent [19]
Hardy et al.

[11] Patent Number: 6,073,629
[45] Date of Patent: Jun. 13, 2000

[54] INHALER SPACER

[75] Inventors: John Graham Hardy, Dunmow, United Kingdom; Lei Mao, Harlow, China; Nick Smalley, Harlow, United Kingdom; Brian David Barney, Gamlingay Sandy, United Kingdom; Vijay Patel, Loughborough, United Kingdom

[73] Assignee: Norton Healthcare Ltd., Essex, United Kingdom

[21] Appl. No.: 09/160,813

[22] Filed: Sep. 25, 1998

Related U.S. Application Data

[60] Provisional application No. 60/060,027, Sep. 25, 1997.

[51] Int. Cl.[7] ................................. A61M 15/00
[52] U.S. Cl. ....................... 128/203.15; 128/203.12
[58] Field of Search ................... 128/203.15, 203.18, 128/203.19, 203.21, 203.12, 200.14, 200.17, 200.18, 200.22; 604/58

[56] References Cited

U.S. PATENT DOCUMENTS

| | | | |
|---|---|---|---|
| 4,841,964 | 6/1989 | Hurka et al. | 128/203.15 |
| 5,203,323 | 4/1993 | Tritle | 128/200.23 |
| 5,458,135 | 10/1995 | Patton et al. | 128/200.14 |
| 5,476,093 | 12/1995 | Lankinen | 128/203.15 |
| 5,505,196 | 4/1996 | Herold et al. | 128/203.15 |
| 5,676,130 | 10/1997 | Gupte et al. | 128/203.19 |
| 5,875,776 | 3/1999 | Vaghefi | 128/203.15 |

FOREIGN PATENT DOCUMENTS

| | | |
|---|---|---|
| 0 475 257 | 3/1992 | European Pat. Off. . |
| WO90/15635 | 12/1990 | WIPO . |
| WO 94/14492 | 7/1994 | WIPO . |

OTHER PUBLICATIONS

Spacer Devices Used With Metered–Dose Inhalers Breakthrough or Gimmick, Peter Konig, M.D., Ph.D. (pp. 276–284).

*Primary Examiner*—Aaron J. Lewis
*Assistant Examiner*—Teena Mitchell
*Attorney, Agent, or Firm*—Darby Darby

[57] ABSTRACT

A spacer for use with a powdered medicament inhaler. The spacer comprises a slender curved body, which defines a chamber, an inlet communicating with the chamber and an outlet communicating with the chamber. The inlet and outlet are adapted to provide a rotational flow path in use for an airstream passing from the inlet through the chamber to the outlet. This selectively extracts particles of powdered medicament entrained in the airstream.

14 Claims, 5 Drawing Sheets

INHALER SPACER

This patent application claims the priority of U.S. provisional patent application Ser. No. 60/060,027, Sep. 25, 1997, which is incorporated herein by reference.

BACKGROUND OF THE INVENTION

1. Field of the Invention

The present invention relates to a spacer for use with an inhaler for dispensing powdered medicament. Such a spacer may be used to ensure that an effective dose of a discrete amount of medicament is dispensed by the inhaler by reducing drug particles above a predetermined size from the administered dose.

2. Discussion of the Related Art

Conventionally dry powder inhalers comprise three parts: a reservoir for solid medicament either in a dry powder form or in a form suitable for the generation of dry powder for delivery on demand; a metering device for delivery of consistent doses of medicament from the reservoir; and an outlet.

A patient inhaling through the outlet receives a metered dose of the medicament. Metered dose inhalers allow the patient to administer an accurate does of medicament when required. This is particularly useful during a sudden occurrence of respiratory difficulty, such as an asthma attack.

One problem with dry powder inhalers is to ensure that an effective dose of the medicament is delivered to the patient's lungs. Dispensed medicament particles tend to separate according to size under the influence of gravity and air currents. Smaller particles, for example less than 5–6 μm in diameter, pass through the patient's oro-pharynx and enter the trachea, bronchi and lower airways where they are able to exert a therapeutic effect. Larger diameter particles are more likely to be deposited in the patient's oro-pharynx. Such oro-pharyngeal deposition is undesirable for a number of reasons. The patient may experience an unpleasant taste when particles alight on the mucosa. Furthermore the proportion of the dispensed dose inhaled which actually constitutes an effective dose is reduced. Moreover unwanted deposits of certain classes of compounds may cause undesirable side effects, eg a high incidence of Candida infections ("thrush") has been reported in association with the administration of corticosteroids.

In pressurised metered dose inhalers the larger droplets formed in the aerosol cloud have been separated out by providing a "large volume spacer" to allow these larger droplets to impinge on the spacer wall, evaporate or fall to the floor of the spacer. Such a "large volume spacer" is unsuitable for use with a powder inhaler where the patient's inspirational air flow withdraws the dose from the inhaler.

Alternatively impact surfaces have been used in order to break up the larger particles of medicament. However this requires a tortuous air path. This results in a bulky spacer and increases the inhalation force required for effective drug delivery. It is undesirable to impose a further burden on a patient who is already experiencing respiratory problems.

SUMMARY OF THE INVENTION

The present invention seeks to provide a compact device which reduces the large particle dose without adversely affecting the fine particle dose and hence reduces the amount of oro-pharyngeal deposition of large medicament particles, while allowing self-administration of an effective dose without increasing the respiratory burden on the user.

According to a first aspect of the invention there is provided a powdered medicament inhaler spacer, comprising:

a body defining a chamber;
an inlet communicating with the chamber; and
an outlet communicating with the chamber, in which the chamber, inlet and outlet are adapted to provide a rotational flow path in use for an airstream passing from the inlet through the chamber to the outlet.

In preferred embodiments of the intention the body has a slender curved configuration.

The body may include an internal surface having the configuration of a closed curve. The body is preferably slender, that is of small width relative to its length or height. The body is preferably curved, that is the body may have the shape of a circle, ellipse, ovoid or other closed curve. Alternatively the body may be partially curved, that is with only a section of the body having a curved shape.

The chamber is preferably cylindrical, more preferably a circular cylinder having a horizontal radial axis in use and a continuous curved internal wall with two generally flat sides. Alternatively the cylinder may have the shape of an ellipse, ovoid or other closed curve.

The inlet and outlet communicate with the chamber such that an airstream with powdered medicament entrained in it may pass through the spacer, entering the chamber through the inlet and exiting the chamber through the outlet. The positions of the inlet and outlet are arranged within the chamber such that the airstream has to undergo at least some degree of rotational motion within the chamber in order to pass through the spacer. In preferred embodiments of the invention rotation through 360° occurs within the chamber. The curved form of the body together with the slender form of the body cooperate to constrain the possible flow paths of the airstream so that the only flow path possible is substantially rotational, ie the geometry of the spacer body reduces motion in a direction transverse to the body and induces rotational motion in direction parallel to the curvature of the body. The rotational motion in general of the medicament particles causes larger particles to be removed from the airstream.

One particular effect of the rotational motion of the powdered medicament particles entrained in the airstream, is that it causes a centripetal force to act on the particles. The reaction of the centripetal force causes particles to move towards the surface of the chamber. The force acting on the particles is proportional to their mass and consequently the more massive particles, ie those with a greater dimension, experience a greater force and are urged towards the curved surface. As the particles impinge on the internal surface of the walls of the body they tend to adhere to it. In this manner particles above a certain size may be selectively removed from the airstream as it passes through the spacer. Hence, a dose of medicament with particles of the desired smaller sizes may be administered.

The curved body is arranged to induce rotational motion in the airstream without increasing the respiratory effort of the user. The curved body relies on its geometric form to induce a rotational flow path without imparting a sudden change in direction of the airstream flow path. Hence, larger particles are caused to adhere to the inner surface of the chamber. Fragmentation of larger particles may occur releasing further medicament of an inhalable size.

The curved body and chamber may have a transverse or radial axis and a lateral axis. Preferably the dimension of the transverse axis is less than the dimension of the lateral axis, more preferably half the dimension of the lateral axis. The transverse, ie radial dimension of the body is less than the lateral dimension of the body so that the flow path of the airstream is constrained to be substantially rotational. The sides of the body are disposed sufficiently close together so as to prevent substantial transverse flow, but are sufficiently spaced apart as to provide the chamber with a shape that does not significantly impede the passage of an airstream through the spacer so that the spacer does not impose a respiratory burden on the user.

The flow within the spacer may be observed in conventional manner using smoke or other opaque gaseous medicine within a spacer constructed of transparent material.

Preferably, the inlet engages the curved body in a first direction and the outlet engages the body in a second direction and the first direction arid the second direction lie in a common plane of the curved body which is perpendicular to the transverse axis. In this way, the inlet and outlet are arranged so that they are coplanar and their common plane is substantially perpendicular to the transverse axis of the body. Hence, only those particles undergoing rotational motion rather than transverse motion will be able to pass from the inlet to the outlet. The first direction and the second direction may be parallel.

In certain embodiments of the invention the inlet tangentially engages the curved body or enters the body tangential to the flow path within the chamber. In this way the airstream enters the chamber and is caused to follow a rotational flow path without having to undergo an abrupt change in direction which may cause the impedance of the spacer to air flow to increase. The outlet preferably also tangentially engages the curved body.

In one embodiment the inlet and outlet do not extend within the chamber. This serves to ensure that the inlet and outlet are flush with the inner surface with the flow of the airstream. This reduces turbulence and may avoid unnecessary surfaces to which particles may adhere.

Alternatively one or both of the inlet or the outlet extend within the chamber. In this way the position within the chamber at which the airstream is introduced, or the position at which the airstream leaves the chamber may be selected. This serves to facilitate the delivery of medicament particles within a selected range of sizes to the patient. However, the ends of the inlet and the outlet need not overlap if the distance between them is such that the momentum of the medicament particles in the airstream is sufficient to prevent any direct non-rotational flow from the inlet to the outlet.

The end of the inlet within the chamber and the end of the outlet within the chamber may co-terminate. Preferably the end of the inlet within the chamber and the end of the outlet within the chamber overlap. The relative positions of the ends of the inlet and outlet within the chamber may be chosen so as to enhance the removal of medicament particles above a selected size from the airstream.

One or more internal surfaces of the body may be roughened so as to facilitate deposition of the unwanted larger particles. In this way the effectiveness of the spacer in selectively removing larger medicament particles may be increased.

The selectively extracted particles may be larger than a predetermined size. Preferably, the predetermined size is about 10 μm, more preferably about 6 μm, most preferably about 2 μm.

An end of the inlet external to the chamber may be adapted to connect to a medicament delivery outlet of the powdered medicament inhaler. An end of the outlet external to the chamber may include a mouthpiece.

The inlet or outlet may have spirals or other moldings inside to give greater turbulence to the airflow.

The spacer may be made wholly or partially of a transparent material. In this way a user can tell when the spacer needs cleaning owing to an excessive build up of extracted medicament. The spacer may be constructed from two parts adapted to allow the spacer to be easily disassembled for cleaning and reassembled for use. This allows the spacer to be easily cleaned so that optimum performance may be maintained and also ensures that the correct effective dose of medicament is delivered.

The spacer may have one or more protuberances extending transversely across the chamber. The presence of the formation in the chamber will help to induce further turbulence in the airstream passing through the spacer and hence increase the amount of medicament selectively extracted from the airstream.

The protuberances may comprise a plurality of stepped baffles disposed on the side walls of the chamber. The stepped baffles may be opposed so as to form constrictions to the airflow. Alternatively the baffles may be disposed in an alternate relationship so that the airflow is caused to pass alternately from one side of the chamber to the other.

Triangular or wedge shaped baffles may be preferred. These may be arranged to extend inwardly from the planar faces of the cylindrical chamber. The baffles may be arranged either clockwise or anti-clockwise so that the airstream contacts the inclined surface or axially extending surface as desired in order to induce the selected degree of turbulence.

When the spacer is constructed from two parts, the formation may include a fastener to secure the two halves of the spacer together. The fastener may be in the form of a screw co-operating with a thread in part of the formation associated with one of the two parts. The screw may be separate to the formation or an integral part of the formation associated with the other of the two parts of the spacer. Alternatively, the fastener may be in the form of a releasable snap-fit device.

The spacer may be integral with the powder dispenser.

According to a second aspect of the invention there is provided a powdered medicament inhaler including a spacer comprising;

a slender curved body defining a chamber;

an inlet communicating with the chamber; and an outlet communicating with the chamber, in which the inlet and the outlet are arranged so that in use an airstream passing from the inlet through the chamber to the outlet is caused by the slender curved body to follow a rotational flow path so as to selectively extract particles of powdered medicament entrained in the airstream.

BRIEF DESCRIPTION OF THE SEVERAL VIEWS OF THE DRAWINGS

The invention will now be further described by means of example, but not in any limiting sense, with reference to the accompanying drawings, in which.

DETAILED DESCRIPTION OF THE INVENTION

Figure 1:
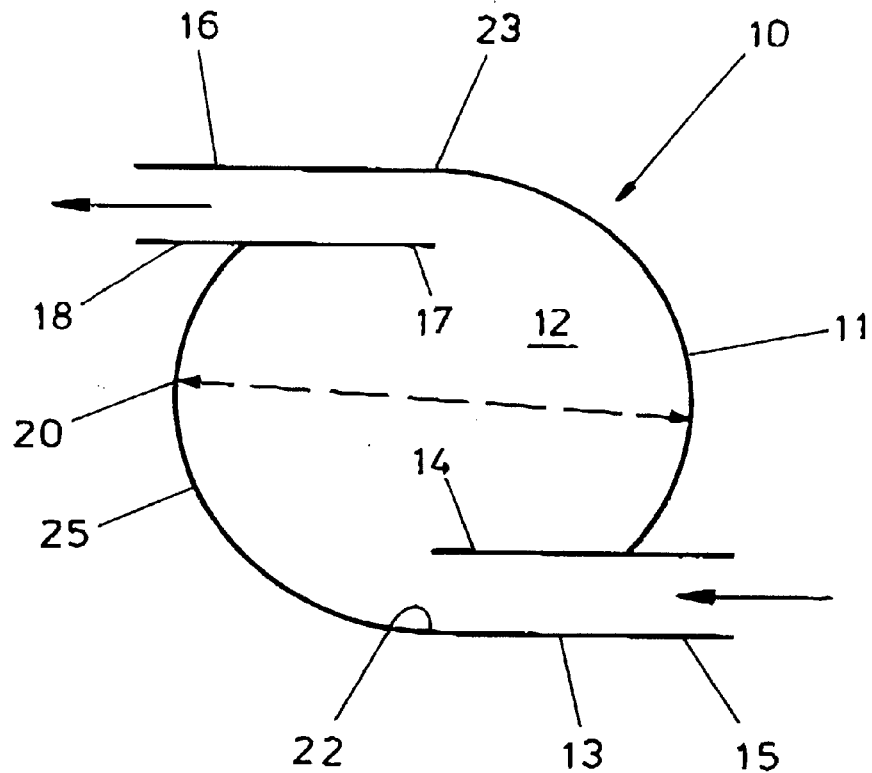
FIG. 1 shows a schematic cross-section of a spacer in accordance with this invention.
Figure 2:
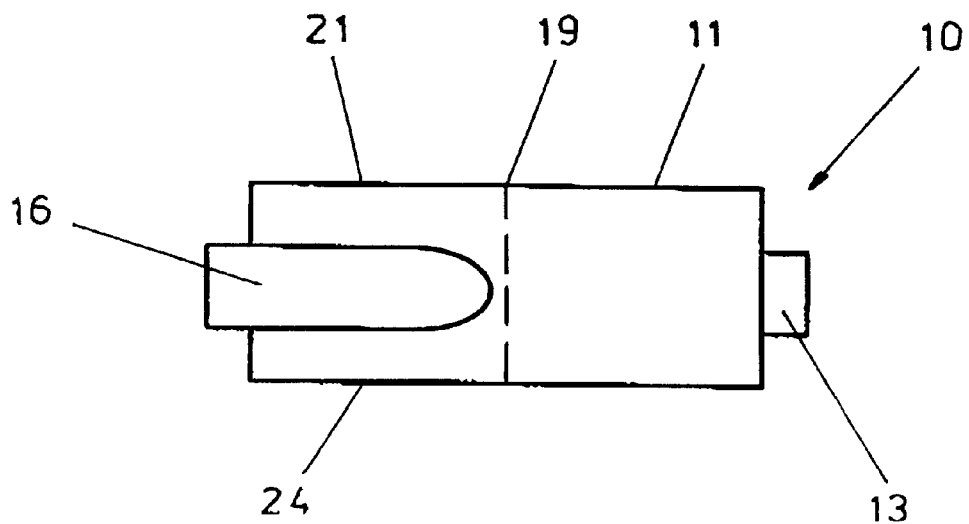
FIG. 2 shows a plan view of the spacer of FIG. 1.

With reference to FIGS. 1 and 2, there is shown a spacer, generally designated by reference numeral 10, for use with a powdered medicament inhaler. The spacer has a right cylindrical body 11, with side walls 21, 24 and curved wall 25, defining a cavity 12. The spacer has an inlet 13 with an end 14 within the chamber and an end 15 external to the chamber. The spacer has an outlet 16 with an end 17 within the chamber and an end 18 external to the chamber.

The body has a transverse axis 19 extending across the width of the body and a lateral axis 20 extending across the length of the sides 21, 24 of the body. The body is slender; ie the width of the body is small compared to the length of the side of the body.

The inlet tangentially engages the body towards the bottom of the body at point 22 and in a first direction, parallel to the sides 21, 24 of the body. The outlet 16 tangentially engages the body towards the top of the body at point 23 and in a second direction parallel to the side of the body 21 and parallel to the inlet 13. Hence, the inlet and outlet lie in a common plane which is perpendicular to the transverse axis 19. The end 14 of the inlet and the end 17 of the outlet co-terminate within the chamber; ie the ends terminate diametrically opposite each other.

The spacer may be constructed from two parts adapted to allow the spacer to be disassembled and reassembled and may be made of a wholly or partially transparent material. this permits the user to easily determine when the spacer needs cleaning and facilitates cleaning of the spacer.

Use of the spacer with a powdered medicament inhaler will now be described. The spacer is connected to a medicament delivery outlet of a powdered medicament inhaler by the end 15 of the inlet 13. A metered dose of powdered medicament is dispensed from the inhaler into the spacer by the user inhaling from the end 18 of the outlet. An airstream with powdered medicament entrained in it flows into the chamber via the inlet. The curvature of the inner surface of the wall of the body causes the airstream flow path to be predominantly circular and to follow a path parallel to the curved wall 25 of the body. The side walls 21, 24 act to restrict any flow along the transverse axis and so co-operate with the curved wall 25 to induce a rotational flow path for the airstream in a clockwise direction.

As the medicament particles entrained in the airstream are undergoing rotational motion, a centripetal force acts upon them. The centripetal force is proportional to their mass and hence size. The reaction to the centripetal force (the imaginary "centrifugal force") causes the particles to move towards the inner surface of the curved wall 25 of the body. However, only those particles of sufficient mass will experience a force of sufficient magnitude to displace them from the airstream. Hence particles above certain size will be selectively extracted from the airstreams and impinge on the roughened internal surface of the cursed wall and accrete to it. This results in the remaining particles entrained in the airstream being of the desired size. These are then ingested by the user via the outlet 16 allowing the correct effective dose to be delivered to the user.

Locating the outlet at the top of the body helps to prevent the ingestion of any large medicament particles which may accumulate at the bottom of the spacer under the action of gravity and otherwise be inadvertently inhaled.

Figure 3:
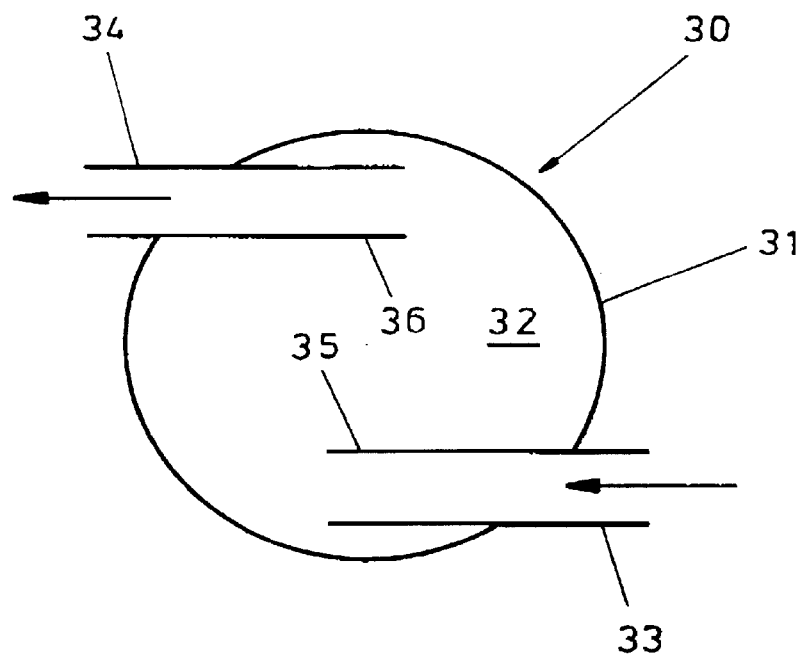
FIG. 3 shows a schematic cross-sectional view of a modified spacer.
Figure 4:
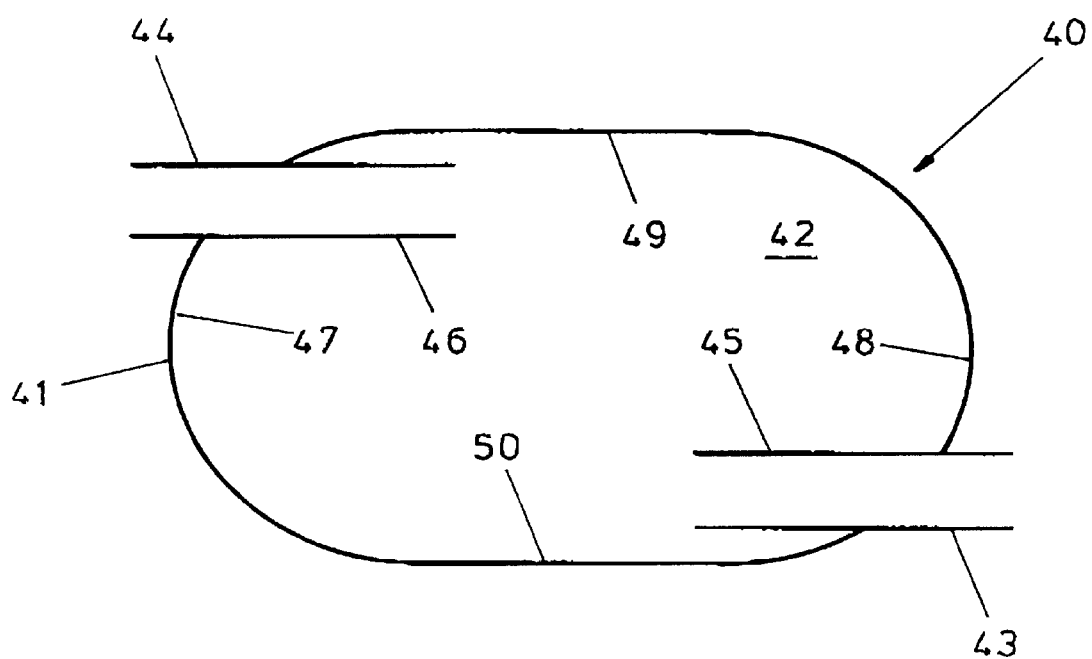
FIG. 4 shows a schematic cross-sectional view of a modified spacer.

A modified spacer will now be described with reference to FIG. 3. The spacer, generally designated by reference number 30, comprises a right cylindrical slender body 31 defining a chamber 32. the spacer has an inlet 33 and an outlet 34 communicating with the chamber 32. An end of the inlet 35 within the chamber and an end of the outlet 36 within the chamber overlap within the chamber; ie the ends of the inlet and outlet overlap in as much as the ends do not terminate at diametrically opposite positions within the chamber.

The spacer 30 works in a similar manner to that for the spacer 10. However, as the ends overlap, the airstream must undergo some several within the chamber, ie a flow path with some rotational component, before it can enter the outlet. Further as the end 36 of the outlet is displaced away from the curved wall of the spacer it is less likely to allow particles deposited on the wall to be inhaled, and rather is positioned well within an area of free rotational flow; ie a position in the flow path where particles of the desired dimensions are more likely to be entrained.

A further modified spacer will now be described with reference to FIG. 4. The spacer, generally designated by reference numeral 40, has a body 41, defining a chamber 42. the spacer has an inlet 43 with an end 45 within the chamber and an outlet 44 with an end 46 within the chamber. The body is slender having a width small relative to the dimensions of its sides. The body has two curved end wall portions 47, 48 joined by two straight wall portions 49, 50, The end 45 of the inlet and the end 46 of the outlet do not overlap within the chamber; ie there is a gap, extending in the direction parallel to the inlet and outlet, between the ends of the inlet and outlet.

In use the spacer works in a similar manner as to that of spacers 10 and 30 described previously, except the relatively increased volume allows for a freer airstream flow.

Regardless of whether the spacer configuration shown in FIGS. 1, 3 or 4 is adopted, the invention still maintains a high fine particle fraction in the dose delivered to the patient's lungs while suppressing the instance of oropharyngeal deposition of the larger particles.

Table 1 shows a comparison for a dry powder inhaler dispensing 400 $\mu$m doses of powdered medicament with no spacer and with various spacers conforming to the current invention. It will be seen from Table 1 that a spacer according to the present invention provides a high respirable fraction of fine particles whilst the deposition of large particles in undesired regions is significantly reduced.

The equipment used was an astra draco four stage liquid impinger manufactured by Copley Instruments of Nottingham, England.

TABLE 1

Drug Dispersion from Budesonide MDPIs (400 $\mu$g/dose) with and without Spacer

| | No Spacer | Spacer A | Spacer B | Spacer C |
|---|---|---|---|---|
| TD ($\mu$g) | 383 | 334 | 346 | 372 |
| FD ($\mu$g) | 191 | 133 | 129 | 130 |

TABLE 1-continued

Drug Dispersion from Budesonide MDPIs (400 μg/dose) with and without Spacer

|  | No Spacer | Spacer A | Spacer B | Spacer C |
|---|---|---|---|---|
| FT (%) | 47 | 14 | 7 | 15 |
| FF (%) | 50 | 40 | 37 | 35 |

TD: Total Dose per Shot
FT: Fraction of Drug at Throat and Stage 1
(Normally larger than 8 μm)
FD: Fine Particle Dose
FF: Fine Particle Fraction
(Normally smaller than 6 μm)

Figure 5A:
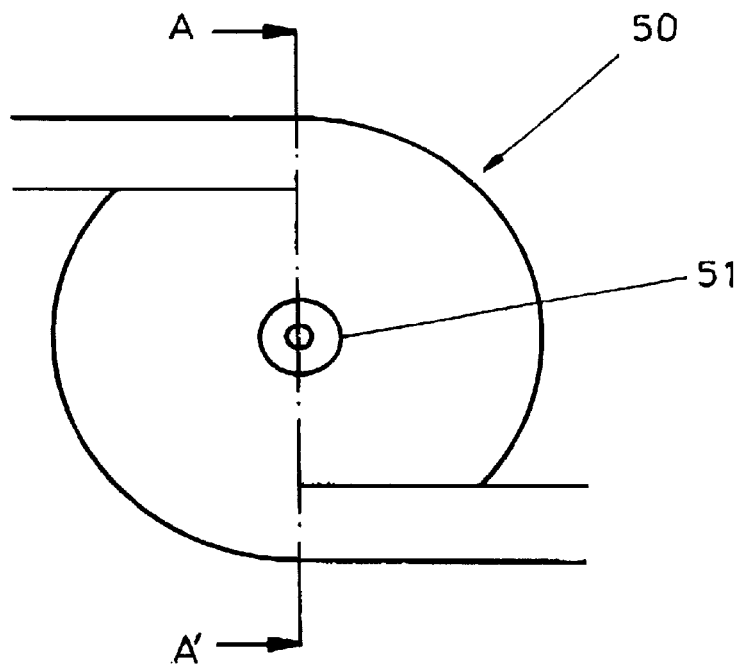
FIGS. 5a and 5b show a first schematic cross-sectional view and a second schematic cross-sectional view along the line AA' respectively of the modified spacer.
Figure 5B:
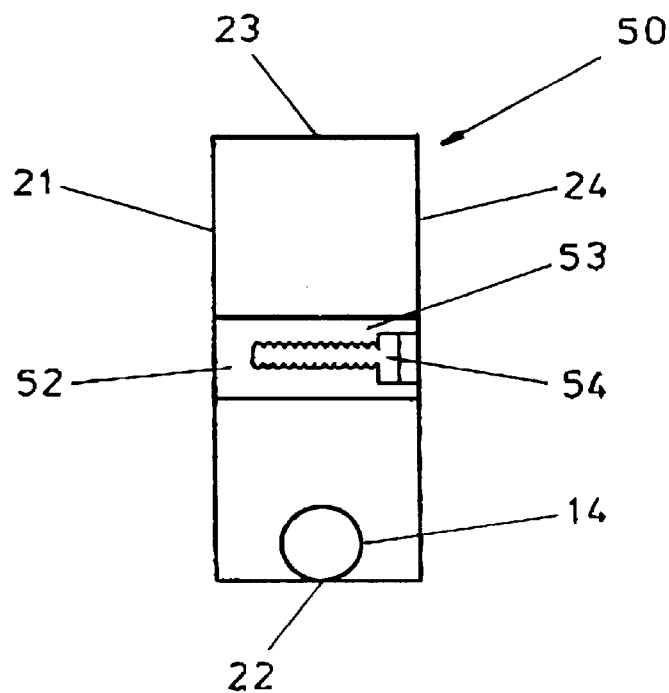

With reference to FIGS. 5a and 5b there is shown a further modified spacer, generally designated by reference numeral 50. The spacer is similar to that shown in FIG. 1, but has a formation 51 which extends transversely across the chamber. The formation acts to induce further turbulence in the airstream as it passes through the chamber and so enhances the selective extraction of medicament from the airstream.

Figure 6:
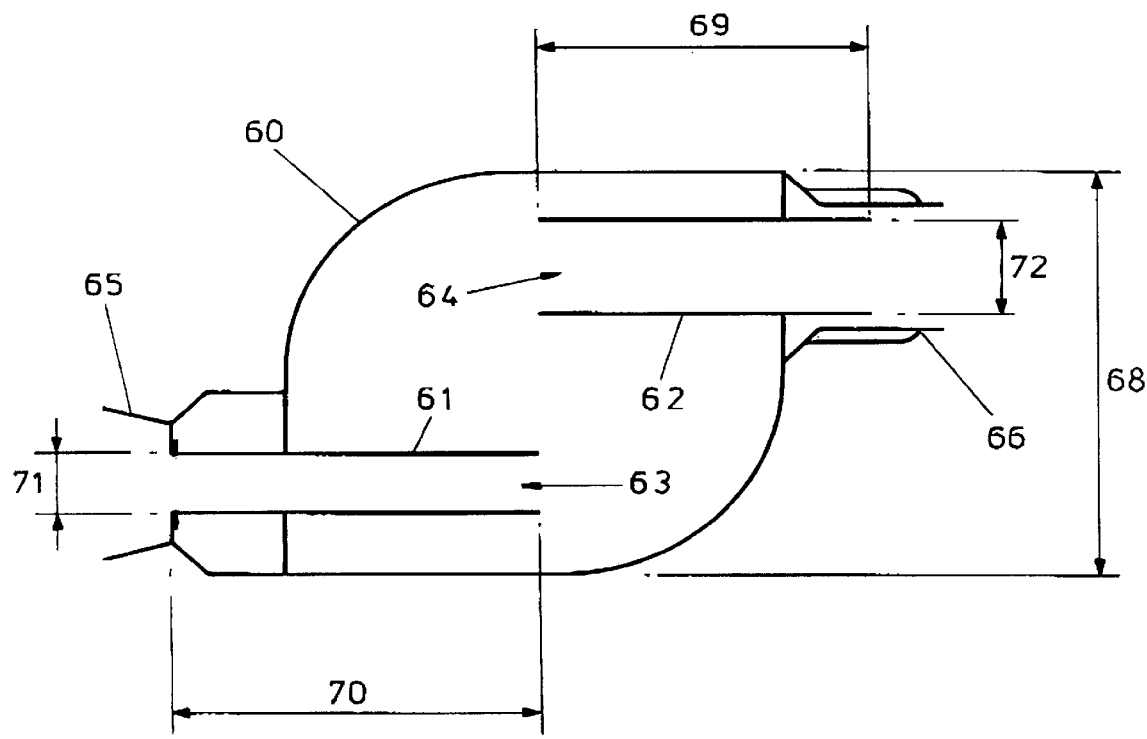
FIG. 6 illustrates the dimension of a spacer in accordance with this invention.
Figure 7:
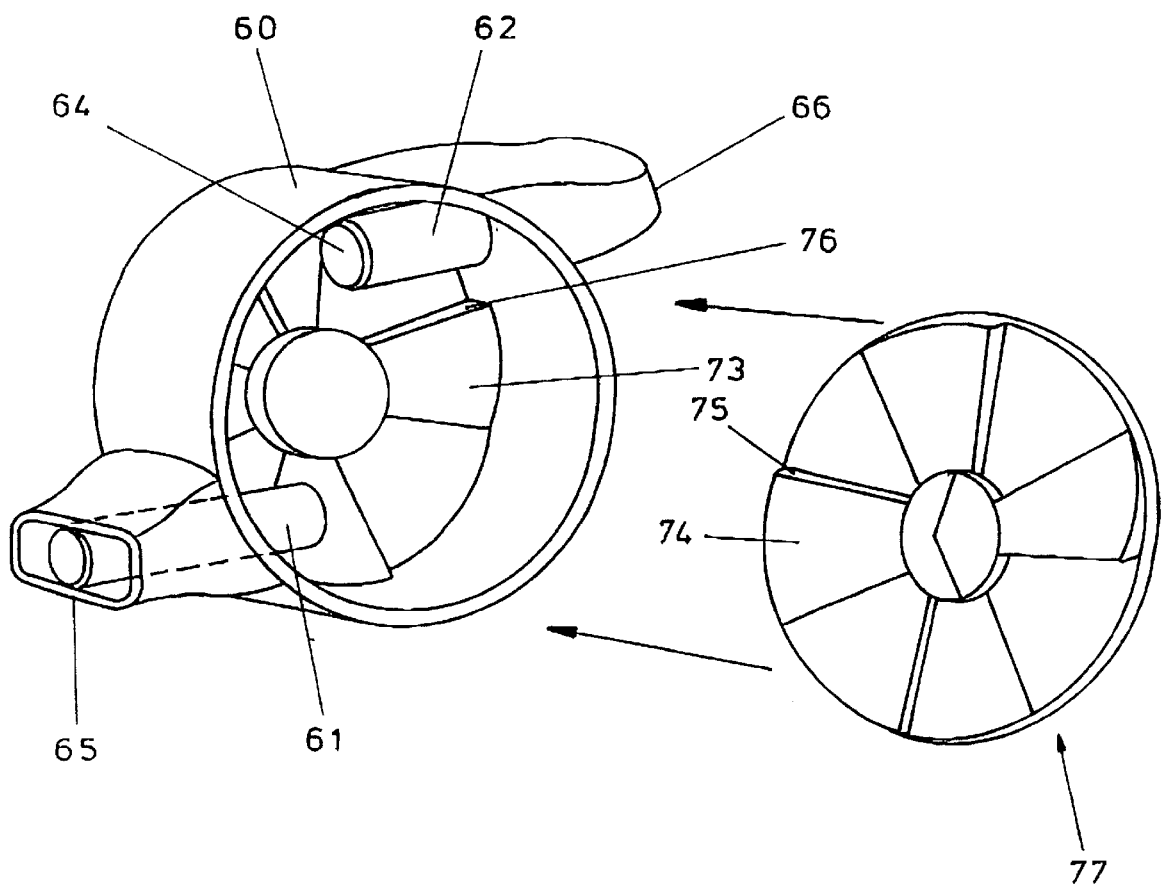
FIG. 7 is a perspective view of a spacer in accordance with this invention.

FIGS. 6 and 7 illustrate a preferred embodiment of the invention. FIG. 7 is a perspective view of the spacer, the dimensions of which are described with reference to FIG. 6.

The spacer has a circular cylindrical body 60 and tubular inlet 61 and outlet 62 arranged generally tangentially parallel to the cylinder 60. The opening 63 of the inlet 61 and entrance 64 to the outlet 62 may be adjusted by movement of the inlet 61 and outlet 62 within their housings. Accordingly the inlet length 70 and outlet length 69 may be adjusted. The inlet and outlet lengths may be adjusted so that the openings 63, 64 lie within the same plane or may extend further so that they overlap preventing direct flow of a particulate containing airstream between the openings 63, 64 without rotation within the chamber 60. The inlet diameter 71 is greater than the outlet diameter 72 to minimise the resistance afforded to a user. The cyclone diameter 68 of the chamber 60 was maintained at 48 mm in the following example.

Wedge shaped baffles 73, 74 are arranged on the planar sides of the spacer. The baffles 73, 74 may be arranged with the axially extending surfaces 75, 76 disposed either facing or away from the direction of air flow as required to afford a desired degree of turbulence within the airstream. The baffles may be arranged to form a series of constrictions as shown in FIG. 7 or alternatively may be arranged to present parallel faces to the airstream to induce oscillations in an axial direction during rotation of the airflow around the chamber.

An axial pillar may be provided to impede direct flow between the inlet 61 and outlet 62.

Tables 2 and 3 illustrate particle sizes obtained from several lengths of inlet and outlet tube and configurations of baffles. Reduction of larger sized particles was observed within the airstream and ministered to a patient.

The equipment used was an astra draco four stage liquid impinger manufactured by Copley Instruments of Nottingham, England. This equipment measures the aerodynamic particle size. Each stage of the impinger has a particular size cut-off and only particles of defined sizes are captured in each stage. The fine particle dose is the mass of drug captured in stages 3 and 4.

Preferred designs have as large as possible reduction in large particle dose (typically greater than 60%) with as small as possible reduction in fine particle dose (typically less than about 15%). Referring to tables 2 and 3, Design 1 exhibited a reduction of 60% of larger particles and only 16% of smaller particles. Design 7 had a reduction of 61% of larger particles and only 12% of smaller particles. Design 8 had a reduction of 58% of larger particles and only 15% of smaller particles.

TABLE 2

| Design No | Inlet Tube (1) | Outlet Tube (1) | Modified Outlet | Modification to Inside of Spacer | |
|---|---|---|---|---|---|
| 1 | 47.5 mm | 42.5 mm | N | Sloping Baffles | (Opposite Rotation) |
| 2 | 47.5 mm | 42.5 mm | N | Axial Pillar | |
| 3 | 47.5 mm | 42.5 mm | Y | Sloping Baffles | (Opposite Rotation) |
| 4 | 47.5 mm | 48.0 mm | N | Sloping Baffles | (Opposite Rotation) |
| 5 | 52.5 mm | 42.5 mm | N | Sloping Baffles | (Opposite Rotation) |
| 6 | 47.5 mm | 32.5 mm | N | Sloping Baffles | (Opposite Rotation) |
| 7 | 47.5 mm | 37.5 mm | N | Sloping Baffles | (Opposite Rotation) |
| 8 | 47.5 mm | 40.0 mm | N | Sloping Baffles | (Opposite Rotation) |
| 9 | 47.5 mm | 37.5 mm | N | Sloping Baffles | (Parallel Rotation (clockwise)) |
| 10 | 47.5 mm | 37.5 mm | N | Sloping Baffles | (Parallel Rotation (anticlockwise)) |
| 11 | 45.0 mm | 37.5 mm | N | Sloping Baffles | (Parallel Rotation (anticlockwise)) |

Notes:
Inlet Diameter = 11.5 mm
Outlet Diameter = 11.0 mm
Spacer Body Internal Diameter = 48 mm

TABLE 3

| Design Number | % Reduction in Fine Particle Dose | % Reduction in Large Particle Dose |
|---|---|---|
| 1 | 16 | 60 |
| 2 | 36 | 71 |
| 3 | 48 | 66 |
| 4 | 29 | 65 |
| 5 | 21 | 58 |
| 6 | 22 | 69 |
| 7 | 12 | 61 |
| 8 | 15 | 58 |
| 9 | 25 | 65 |
| 10 | 27 | 65 |
| 11 | 39 | 63 |

What is claimed is:

1. A powdered medicament inhaler spacer comprising:

a body defining a chamber;

an inlet communicating with the chamber; and an outlet communicating with the chamber, in which the chamber inlet and outlet are adapted to provide a rotational flow path in use for an airstream passing from the inlet through the chamber to the outlet;

wherein one of the inlet and outlet extends into the chamber.

2. A spacer as claimed in claim 1, wherein the body has a slender curved configuration.

3. A spacer as claimed in claim 1 wherein the body includes an internal surface having the configuration of a closed curve.

4. A spacer as claimed in claim 3, wherein the internal surface has the configuration of a circle or ellipse.

5. A spacer as claimed in claim 1, wherein the chamber is cylindrical.

6. A spacer as claimed in claim 1, wherein the inlet and outlet are arranged so that in use the airstream undergoes rotation through 360° within the chamber.

7. A spacer as claimed in claim 1, wherein the inlet engages the curved body in a first direction and the outlet engages the body in a second direction and wherein the first direction and the second direction lie in a common plane perpendicular to a transverse axis of the curved body.

8. A spacer as claimed in claim 1 wherein the inlet and outlet are coplanar.

9. A spacer as claimed in claim 8, wherein the common plane is perpendicular to the transverse axis of the body.

10. A spacer as claimed in claim 8, wherein the inlet and outlet are parallel.

11. A spacer as claimed in claim 1, wherein the inlet and outlet do not extend into the chamber.

12. A spacer as claimed in claim 1, wherein the ends of the inlet and outlet overlap.

13. A spacer as claimed in claim 1, including one or more baffle formations extending transversely across the chamber to induce turbulence into the airstream in use.

14. A spacer as claimed in claim 1, including a pillar extending axially across the chamber.

* * * * *

UNITED STATES PATENT AND TRADEMARK OFFICE
CERTIFICATE OF CORRECTION

PATENT NO.   : 6,073,629
DATED        : June 13, 2000
INVENTOR(S)  : John Graham Hardy et al.

It is certified that errors appear in the above-identified patent and that said Letters Patent is hereby corrected as shown below:

Title page, [75] Inventors: please change the following information as follows:

"Lei Mao, Harlow, China" to -- Lei Mao, Harlow, United Kingdom; "Brian David Barney, Gamlingay, Sandy, United Kingdom" to -- David Brian Barney, Bishops Stortford, United Kingdom --.

Signed and Sealed this

Twenty-second Day of May, 2001

Attest:

NICHOLAS P. GODICI

*Attesting Officer*       Acting Director of the United States Patent and Trademark Office